United States Patent
Bizup et al.

(10) Patent No.: US 8,608,712 B2
(45) Date of Patent: Dec. 17, 2013

(54) SEPTUM FOR VENOUS ACCESS PORT ASSEMBLY

(75) Inventors: Raymond Bizup, Feasterville, PA (US); Kevin Sanford, Chalfont, PA (US); Timothy Schweikert, Levittown, PA (US)

(73) Assignee: Medical Components, Inc., Harleysville, PA (US)

( * ) Notice: Subject to any disclaimer, the term of this patent is extended or adjusted under 35 U.S.C. 154(b) by 1714 days.

(21) Appl. No.: 11/803,490

(22) Filed: May 11, 2007

(65) Prior Publication Data

US 2007/0276344 A1 Nov. 29, 2007

Related U.S. Application Data

(60) Provisional application No. 60/802,340, filed on May 22, 2006.

(51) Int. Cl.
*A61M 37/00* (2006.01)

(52) U.S. Cl.
USPC .................................................. 604/288.02

(58) Field of Classification Search
USPC ............... 604/167.02, 891.1, 288.01–288.04
See application file for complete search history.

(56) References Cited

U.S. PATENT DOCUMENTS

| D44,302 S | 7/1913 | Director |
|---|---|---|
| D130,852 S | 12/1941 | Rothschild |
| 4,559,043 A | 12/1985 | Whitehouse et al. |
| 4,673,394 A | 6/1987 | Fenton, Jr. et al. |
| 4,681,560 A | 7/1987 | Schulte et al. |
| 4,692,146 A | 9/1987 | Hilger |
| 4,695,273 A | 9/1987 | Brown |
| 4,704,103 A | 11/1987 | Stober et al. |
| 4,710,167 A | 12/1987 | Lazorthes |
| 4,762,517 A * | 8/1988 | McIntyre et al. ............. 604/175 |
| 4,772,270 A | 9/1988 | Wiita et al. |
| 4,778,452 A | 10/1988 | Moden et al. |
| 4,781,680 A | 11/1988 | Redmond et al. |
| 4,802,885 A | 2/1989 | Weeks et al. |
| 4,886,501 A | 12/1989 | Johnston et al. |
| 4,892,518 A | 1/1990 | Cupp et al. |
| 4,904,241 A | 2/1990 | Bark |

(Continued)

FOREIGN PATENT DOCUMENTS

| EP | 1 238 682 | 9/2002 |
|---|---|---|
| JP | 63-38535 | 3/1988 |

(Continued)

OTHER PUBLICATIONS

International Search Report dated Aug. 28, 2008, PCT/US07/11456 (4 pages).

(Continued)

*Primary Examiner* — Nicholas Lucchesi
*Assistant Examiner* — Nathan R Price
(74) *Attorney, Agent, or Firm* — Blank Rome LLP

(57) ABSTRACT

A venous access port assembly having a housing with a discharge port, and a needle-penetrable septum. An interior reservoir is defined in the assembly, and a passageway extends from the reservoir through the discharge port. The needle access area of the septum includes a tactilely identifiable differentiation along the top surface thereof, such as a ridge, a recess, an X-shaped protrusion, a V-shaped groove, or a bipartite dome.

17 Claims, 3 Drawing Sheets

(56) References Cited

U.S. PATENT DOCUMENTS

| | | |
|---|---|---|
| 4,915,690 A | 4/1990 | Cone et al. |
| 5,013,298 A | 5/1991 | Moden et al. |
| 5,045,060 A | 9/1991 | Melsky et al. |
| 5,084,015 A | 1/1992 | Moriuchi |
| 5,108,377 A | 4/1992 | Cone et al. |
| 5,137,529 A | 8/1992 | Watson et al. |
| 5,167,629 A | 12/1992 | Yertenstein et al. |
| 5,167,638 A | 12/1992 | Felix et al. |
| 5,180,365 A | 1/1993 | Ensminger et al. |
| 5,185,003 A | 2/1993 | Brethauer |
| 5,207,644 A | 5/1993 | Strecker |
| 5,213,574 A | 5/1993 | Tucker |
| 5,263,930 A | 11/1993 | Ensminger |
| D342,134 S | 12/1993 | Mongeon |
| 5,281,199 A | 1/1994 | Ensminger et al. |
| 5,281,205 A | 1/1994 | McPherson |
| 5,318,545 A | 6/1994 | Tucker |
| 5,356,381 A | 10/1994 | Ensminger et al. |
| 5,360,407 A | 11/1994 | Leonard |
| 5,387,192 A | 2/1995 | Glantz |
| 5,399,168 A | 3/1995 | Wadsworth, Jr. et al. |
| 5,476,460 A | 12/1995 | Montalvo |
| 5,503,630 A | 4/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,593,028 A | 1/1997 | Haber et al. |
| 5,607,393 A | 3/1997 | Ensminger et al. |
| 5,613,945 A | 3/1997 | Cai et al. |
| 5,620,419 A | 4/1997 | Lui et al. |
| 5,637,102 A | 6/1997 | Tolkoff et al. |
| 5,713,858 A | 2/1998 | Heruth et al. |
| 5,718,682 A | 2/1998 | Tucker |
| 5,743,873 A | 4/1998 | Cai et al. |
| 5,792,104 A | 8/1998 | Speckman et al. |
| 5,833,654 A | 11/1998 | Powers et al. |
| 5,848,989 A | 12/1998 | Villani |
| 5,951,512 A | 9/1999 | Dalton |
| 5,989,216 A | 11/1999 | Johnson et al. |
| 6,086,555 A | 7/2000 | Eliasen et al. |
| 6,090,066 A | 7/2000 | Schnell |
| 6,113,572 A | 9/2000 | Gailey et al. |
| 6,190,352 B1 | 2/2001 | Haarala et al. |
| 6,213,973 B1 | 4/2001 | Eliasen et al. |
| 6,503,228 B1 | 1/2003 | Li et al. |
| 6,527,754 B1 | 3/2003 | Tallarida et al. |
| 6,562,023 B1 | 5/2003 | Marrs et al. |
| D480,942 S | 10/2003 | Ishida et al. |
| 6,719,739 B2 | 4/2004 | Verbeek et al. |
| 6,758,841 B2 | 7/2004 | Haarala et al. |
| D498,894 S | 11/2004 | Gould |
| 6,971,390 B1 | 12/2005 | Vasek et al. |
| 6,997,914 B2 | 2/2006 | Smith et al. |
| D518,573 S | 4/2006 | French |
| 7,186,236 B2 | 3/2007 | Gibson et al. |
| D546,440 S | 7/2007 | Burnside |
| D556,153 S | 11/2007 | Burnside |
| D562,443 S | 2/2008 | Zinn et al. |
| D574,950 S | 8/2008 | Zawacki et al. |
| 8,034,032 B2 | 10/2011 | Voegele et al. |
| 2004/0006316 A1 * | 1/2004 | Patton ............................ 604/244 |
| 2005/0077688 A1 | 4/2005 | Voegele et al. |
| 2005/0085778 A1 | 4/2005 | Parks |
| 2005/0171502 A1 | 8/2005 | Daly et al. |
| 2006/0100592 A1 | 5/2006 | Eliasen |
| 2006/0116648 A1 | 6/2006 | Hamatake |
| 2006/0184141 A1 | 8/2006 | Smith et al. |
| 2006/0184142 A1 | 8/2006 | Schon et al. |
| 2006/0217659 A1 | 9/2006 | Patton |
| 2006/0217668 A1 | 9/2006 | Schulze et al. |
| 2006/0224129 A1 | 10/2006 | Beasley et al. |
| 2006/0247584 A1 | 11/2006 | Sheetz et al. |
| 2006/0264898 A1 | 11/2006 | Beasley et al. |
| 2007/0078391 A1 | 4/2007 | Wortley et al. |
| 2007/0078416 A1 | 4/2007 | Eliasen |
| 2007/0185462 A1 | 8/2007 | Byrum |
| 2007/0219510 A1 | 9/2007 | Zinn et al. |
| 2007/0233017 A1 | 10/2007 | Zinn et al. |
| 2007/0255226 A1 | 11/2007 | Tennican et al. |
| 2007/0270770 A1 | 11/2007 | Bizup |
| 2007/0276344 A1 | 11/2007 | Bizup |
| 2008/0140025 A1 | 6/2008 | Sheetz et al. |
| 2008/0319398 A1 | 12/2008 | Bizup |

FOREIGN PATENT DOCUMENTS

| | | |
|---|---|---|
| JP | 2004-350937 | 12/2004 |
| WO | WO94/05351 | 3/1994 |
| WO | WO97/01370 | 1/1997 |
| WO | WO98/55167 | 12/1998 |

OTHER PUBLICATIONS

Written Opinion dated Aug. 28, 2008, PCT/US07/11456 (4 pages).
PCT/US07/11456 International Preliminary Report on Patentability dated May 5, 2010, 6 pages.

* cited by examiner

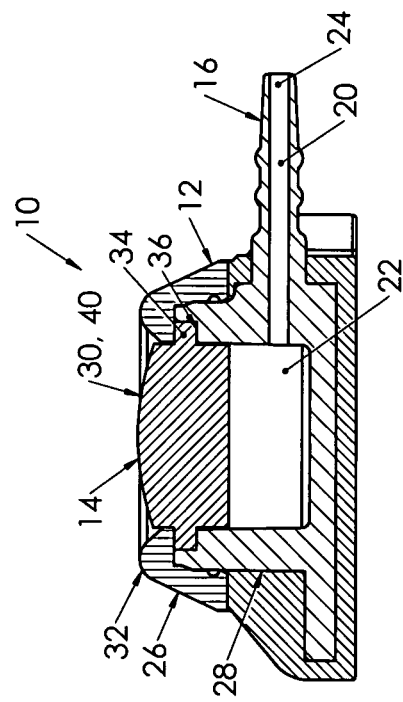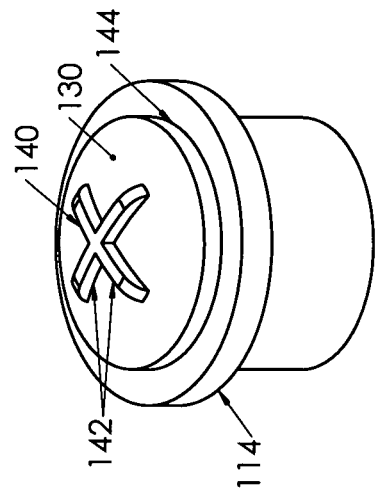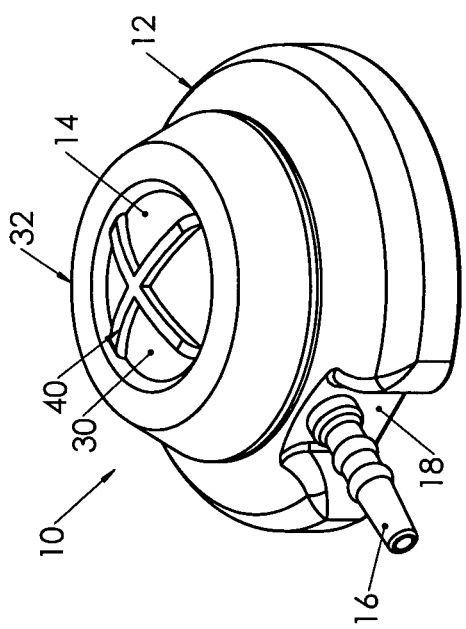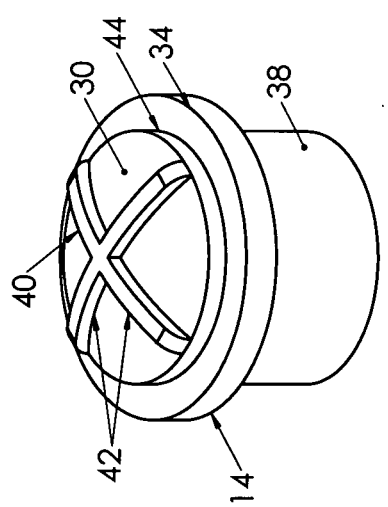

SEPTUM FOR VENOUS ACCESS PORT ASSEMBLY

CROSS-REFERENCE TO RELATED APPLICATIONS

This application claims the benefit of U.S. Provisional Patent Application Ser. No. 60/802,340 filed May 22, 2006.

FIELD OF THE INVENTION

This relates to the field of medical devices and more particularly to venous access ports for catheter systems for the infusion of fluids into a patient and withdrawal of fluids from the patient.

BACKGROUND OF THE INVENTION

Infusion ports for the infusion and/or withdrawal of fluids from a patient are well-known, secured to the proximal end of an implanted catheter. These ports are typically used for drug infusion or small amounts of blood withdrawal, where large flows of fluid are not required. The ports are assemblies of a needle-impenetrable housing with a discharge port in fluid communication with the catheter and the reservoir within the port housing, and provide a subcutaneous self-sealing septum that defines an access site for multiple needle sticks through the covering skin tissue of the patient, through the septum and into the reservoir, without the need to continuously search for new access sites. Examples of such ports are disclosed, for example, in U.S. Pat. Nos. 4,704,103; 4,762,517; 4,778,452; 5,185,003; 5,213,574 and 5,637,102.

The septum conventionally includes a dome-shaped access surface into which the needle is to be inserted. The domed access surface rises upwardly at least as far as the surrounding periphery of the port housing, and conventionally such surface is domed so that a practitioner is easily able to locate the access port and particularly the septum access surface that is subcutaneously placed under the skin of the patient, by palpation. Also, conventionally, the surrounding periphery of the cap serves as a tactilely discernible ring indicating that the septum's access surface is inside thereof. Such palpation is disclosed particularly in U.S. Pat. Nos. 4,772,270 and 5,137,529, and in U.S. Patent Publication No. 2006/0224129 A1.

It is desired to provide a venous access port assembly that provides a more easily discernable needle target identification capability via palpation.

BRIEF SUMMARY OF THE INVENTION

The present invention is a venous access port having a needle-impenetrable housing and a needle-penetrable septum, providing an interior reservoir and a passageway extending from the reservoir through a stem of a discharge port to establish fluid communication with a proximal end of a catheter lumen implanted into a patient. The needle-penetrable septum is secured to the housing, and preferably includes a seating flange of the septum that is held compressibly in a seat in the housing. The present invention comprises a tactile locating feature on the needle-accessible top surface of the septum, enabling the identification of the center of the septum's top surface and that is integral with the septum but tactilely differentiatable along the septum's top surface, that through palpation allows identification of the needle target area and facilitates in denoting the needle target area during palpation.

Embodiments of tactile locating features include large or small X-shaped protrusions or a groove or depression or a ridge, where the top surface of the septum may be generally convex or dome-shaped, and also a bipartite dome embodiment wherein one-half of the septum top surface is half-dome-shaped while the other half has a noticeably lower height or even flat, defining a generally vertical face between the half-dome and the lower half.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIGS. 1 and 2 are an isometric and a cross-sectional view, respectively, of a venous access port assembly containing the septum of the present invention;

FIG. 3 is an isometric view of a first embodiment of the septum of the present invention; and FIGS. 4 to 11 are isometric views similar to FIG. 3 of other embodiments of septa of the present invention.

DETAILED DESCRIPTION OF THE INVENTION

Figure 5:
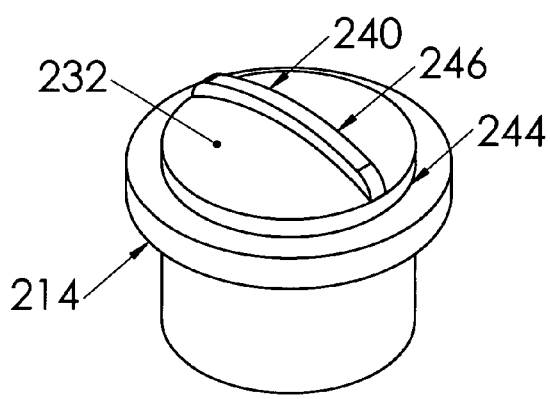

In the drawings, like numerals indicate like elements throughout. Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Venous access port assembly 10 of FIGS. 1 and 2 includes a needle-impenetrable housing 12 and a needle-penetrable septum 14, with a discharge port 16 extending from a distal end 18 of the port assembly 10 to be attached securely and sealingly to the proximal end of a catheter (not shown). A passageway 20 extends from the interior reservoir 22 to the distal tip opening 24 of discharge port 16. A cap 26 secures to housing base 28 and secures the septum within the assembly 10. Septum 14 is made from elastomeric material of appropriately low durometer to permit insertion of a needle thereinto, and is self-sealing upon needle withdrawal. The material of septum 14 is also such as to permit many cycles of needle insertion and withdrawal.

Septum 14 of FIGS. 1 to 3 includes a preferably dome-shaped access surface 30 into which the needle is to be inserted to either inject fluids into the access port and into the patient, or to withdraw small amounts of blood from the patient via the access port. Domed access surface 30 rises upwardly at least as far as the surrounding periphery 32 of the cap 26, and conventionally such surface is domed so that a practitioner is easily able to locate the access port and particularly the septum access surface within the cap periphery that is subcutaneously placed under the skin of the patient, by palpation. Septum 14 also includes a seating flange 34 that is secured within a septum seat 36 of the housing base 28 by the cap upon assembly, preferably simultaneously being placed under vertical compression and horizontal compression to assure sealing by appropriate shaping and dimensioning of the adjacent portions of the seat, flange and cap. The septum further may include a plug section 38 that further assists sealing of reservoir 22 therebeneath upon assembly, and also stabilizes the septum during handling and needle insertion and withdrawal.

As seen best in FIG. 3, septum 14 includes a locator 40 along domed surface 30, that is preferably centered in relationship thereto and preferably is also integral therewith. Locator 40 is of a shape and height that during palpation, the practitioner is particularly able to discern the center of the domed access surface to better identify the access port topography for needle insertion. Locator 40 of FIG. 3 is an X-shape protrusion having legs 42 of limited height and width that extend to rounded ends at the periphery 44 of the septum's access surface 30. Preferably the top surfaces of the legs are curved at their outer ends, and may be flattened from side to side therealong. The locator feature of the present invention will allow better identification by tactile feel of the access or target area for percutaneous needle insertion to access the port.

In FIG. 4, septum 114 includes a locator 140 along domed surface 130 that again is an X-shaped protrusion, as in FIG. 3, but legs 142 of limited height and width that extend to rounded ends only partially toward the domed surface periphery 144.

Figure 6:
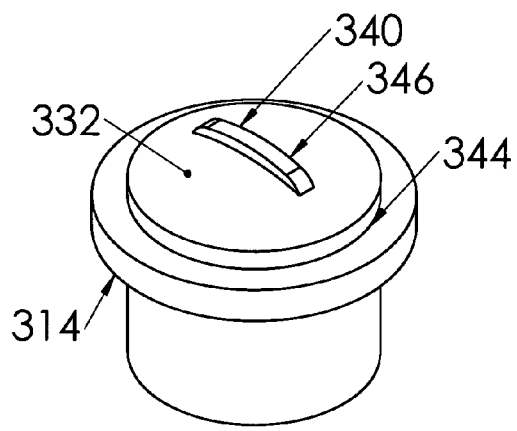

FIGS. 5 and 6 illustrate additional embodiments of septa 214, 314 wherein locators 240, 340 comprise a single ridge 246,346 that traverses the domed surfaces 232,332 to the periphery 244, and only partially to the periphery 344, respectively. Preferably, the ridge extends to rounded ends or may be totally generally rounded, or both, as shown, and may be flattened from side to side therealong.

Figure 7:
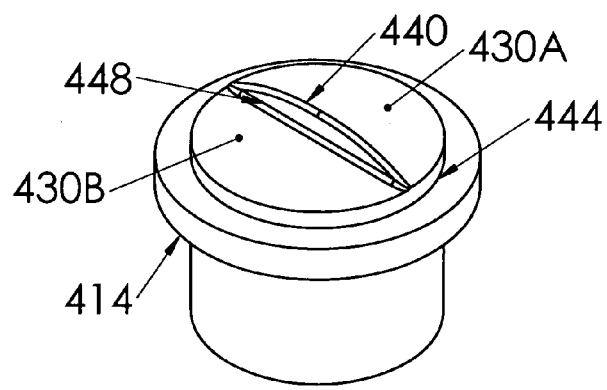

Regarding FIG. 7, septum embodiment 414 has a bipartite domed access surface comprised of a first half-domed surface 430A and a second access surface portion 430B that may be flat as shown, or slightly domed, wherein first half-domed surface protrudes upwardly higher that second access surface portion 430B, forming a vertical offset or face 448.

Figure 8:
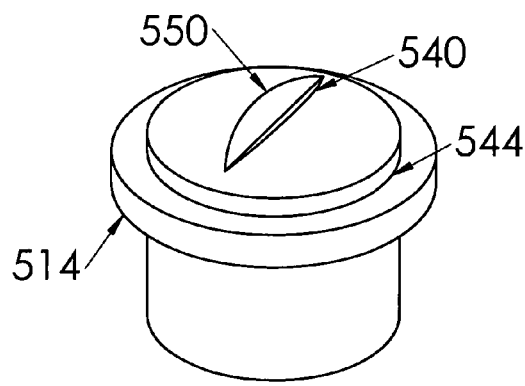

Regarding FIG. 8, septum embodiment 514 is shown to have locator 540 that is a shallow V-shaped groove 550 extending preferably only partially to the periphery 544.

Figure 9:
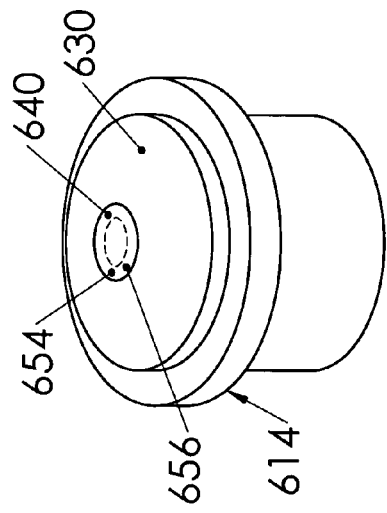

FIG. 9 illustrates a septum embodiment 614 with a dome-shaped needle access area 630 having an indicator 640. The indicator is a depression or recess 654 centered with respect to needle access area 630. Preferably, the recess 654 has a distinctly tactilely noticeably steep periphery 656, but the recess may have a small or large diameter relative to the dome-shaped needle access area 630.

Figure 11:
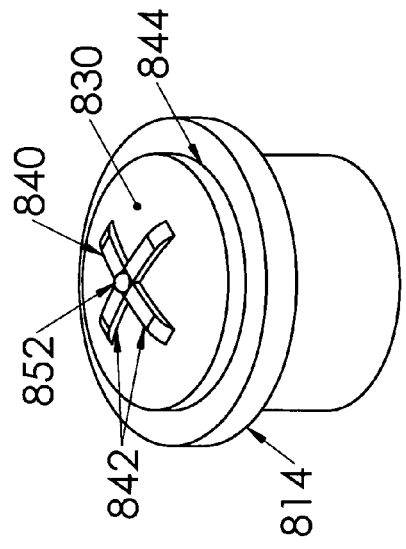
Figure 10:
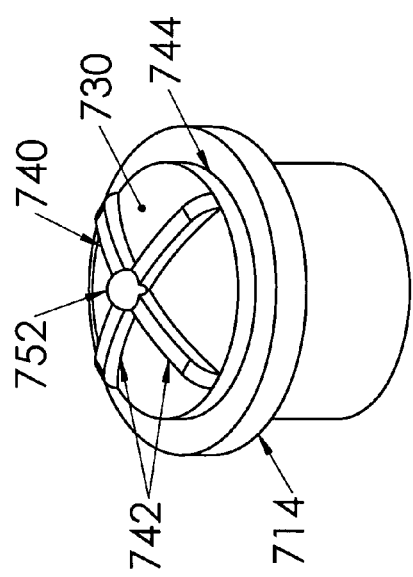

Now referring to FIGS. 10 and 11, septa embodiments 714,814 have locators 740,840 that include an X-shaped protrusion having legs 742,842 that are similar to those of FIGS. 3 and 4 but that further include a centrally located rounded bump or nipple 752,852, respectively, rising higher than the height of the X-shaped protrusion.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. In a needle-penetrable septum for a venous access port assembly having a needle-impenetrable housing with a discharge port for connection and fluid communication with a catheter lumen, and a reservoir defined within the assembly and in fluid communication with the discharge port, the needle-penetrable septum having an exposed needle access area, the improvement comprising:
a tactilely identifiable section on the needle access area thereof but tactilely differentiatable therefrom, that through palpation is adapted to provide identification of the needle target area, wherein the tactilely identifiable section is an X-shaped protrusion having legs of limited width that extend from the center of the needle access area to the periphery thereof, the X-shaped protrusion adapted to provide identification of the exposed needle target area through palpation.

2. The septum of claim 1, wherein the needle access area is dome-shaped.

3. The septum of claim 1, wherein the tactilely identifiable section includes a rounded protrusion extending upwardly from the center of the X-shaped protrusion.

4. The septum of claim 1, wherein top surfaces of the legs are flattened from side to side therealong.

5. A venous access port assembly including the septum of claim 1.

6. In a needle-penetrable septum for a venous access port assembly having a needle-impenetrable housing with a discharge port for connection and fluid communication with a catheter lumen, and a reservoir defined within the assembly and in fluid communication with the discharge port, the needle-penetrable septum having an exposed needle access area, the improvement comprising:
a tactilely identifiable section on the needle access area thereof but tactilely differentiatable therefrom, that through palpation is adapted to provide identification of the needle target area, wherein the tactilely identifiable section is a ridge of limited height and width that extends in opposite directions from the center of the needle access area to the periphery thereof.

7. The septum of claim 6, wherein the needle access area is dome-shaped.

8. The septum of claim 6, wherein the ridge has a curved top surface and extends to rounded ends.

9. The septum of claim 6, wherein a top surface of the ridge is flattened from side to side therealong.

10. A venous access port assembly including the septum of claim 6.

11. In a needle-penetrable septum for a venous access port assembly having a needle-impenetrable housing with a discharge port for connection and fluid communication with a catheter lumen, and a reservoir defined within the assembly and in fluid communication with the discharge port, the needle-penetrable septum having an exposed needle access area, the improvement comprising:
a tactilely identifiable section on the needle access area thereof but tactilely differentiatable therefrom, that through palpation is adapted to provide identification of the needle target area, wherein the tactilely identifiable section is a wedge-shaped recess extending downwardly into the needle access area and is at least disposed centrally of the needle access area.

12. The septum of claim 11, wherein the needle access area is dome-shaped.

13. The septum of claim 11, wherein the recess is a V-shaped groove at least traversing the center of the needle access area.

14. A venous access port assembly including the septum of claim 11.

15. In a needle-penetrable septum for a venous access port assembly having a needle-impenetrable housing with a discharge port for connection and fluid communication with a catheter lumen, and a reservoir defined within the assembly and in fluid communication with the discharge port, the needle-penetrable septum having an exposed needle access area, the improvement comprising:

a tactilely identifiable section on the needle access area thereof but tactilely differentiatable therefrom, that through palpation is adapted to provide identification of the needle target area, wherein the needle access area has a first half that is half-dome-shaped to a selected height and a second half that has a distinctly lesser height.

16. The septum of claim 15, wherein the second half of the needle access area is flat.

17. A venous access port assembly including the septum of claim 15.

\* \* \* \* \*